(12) United States Patent
Cosentino

(10) Patent No.: US 12,283,352 B2
(45) Date of Patent: Apr. 22, 2025

(54) ELECTRONIC COVID, VIRUS, MICROORGANISMS, PATHOGENS, DISEASE DETECTOR

(71) Applicant: Filadelfo Joseph Cosentino, Plano, TX (US)

(72) Inventor: Filadelfo Joseph Cosentino, Plano, TX (US)

(*) Notice: Subject to any disclaimer, the term of this patent is extended or adjusted under 35 U.S.C. 154(b) by 273 days.

(21) Appl. No.: 17/300,114

(22) Filed: Feb. 1, 2021

(65) Prior Publication Data

US 2022/0246249 A1    Aug. 4, 2022

(51) Int. Cl.
*G16C 20/20* (2019.01)
*G16H 50/20* (2018.01)
*G16H 50/30* (2018.01)
*G16H 50/80* (2018.01)

(52) U.S. Cl.
CPC ............. *G16C 20/20* (2019.02); *G16H 50/20* (2018.01); *G16H 50/30* (2018.01); *G16H 50/80* (2018.01)

(58) Field of Classification Search
CPC ........ G16C 20/20; G16H 50/20; G16H 50/30; G16H 50/80
USPC ...................... 435/5, 6.12–6.14; 436/43, 173; 702/19–24, 188
See application file for complete search history.

(56) References Cited

U.S. PATENT DOCUMENTS

| | | | | |
|---|---|---|---|---|
| 8,637,194 B2 * | 1/2014 | Long | .................... | H01M 14/00 429/401 |
| 11,333,648 B1 * | 5/2022 | Ricci | .................... | G01N 27/128 |
| 11,618,875 B2 * | 4/2023 | Papermaster | .......... | G16H 40/63 702/19 |
| 2006/0224332 A1 * | 10/2006 | Johnson | ............. | G01N 33/0031 702/22 |
| 2007/0116607 A1 * | 5/2007 | Wang | ................ | B01L 3/502715 422/83 |
| 2007/0168461 A1 * | 7/2007 | Moore | .................... | G16H 10/60 709/217 |
| 2009/0058072 A1 * | 3/2009 | Weber | .................. | B42D 15/004 604/361 |
| 2013/0029374 A1 * | 1/2013 | Eberheim | ................. | B01L 3/50 436/163 |
| 2015/0257658 A1 * | 9/2015 | Geesbreght | ............ | G16H 50/20 600/301 |
| 2021/0382003 A1 * | 12/2021 | Guzman | .......... | G01N 27/44756 |
| 2023/0200646 A1 * | 6/2023 | Howard | ............... | A61B 5/0002 702/19 |
| 2023/0317285 A1 * | 10/2023 | Yadav | .................... | G16H 50/20 702/19 |

FOREIGN PATENT DOCUMENTS

WO    WO-2022051680 A1 *    3/2022    ........... A61B 5/7225

* cited by examiner

*Primary Examiner* — Jeffrey P Aiello
(74) *Attorney, Agent, or Firm* — Kirby Drake

(57) ABSTRACT

This device will use a combination or existing "on the shelf" technologies for specific use of detecting molecular signatures/molecular fingerprints of COVID, Virus, and all strains of the virus, microorganisms, pathogens, disease, disorders, and cancer by type by sampling the specific odor with an electronic nose, match the molecular signature/molecular fingerprints with digitized odors in a database, and produce alarms audible, audio, and communication alarms with other data regarding a positive match in the database of digitized unique molecular signatures/molecular fingerprints in the database.

13 Claims, 4 Drawing Sheets

Software Architecture Schematic
CPU Display, Communications, Alerts
Subsystem A

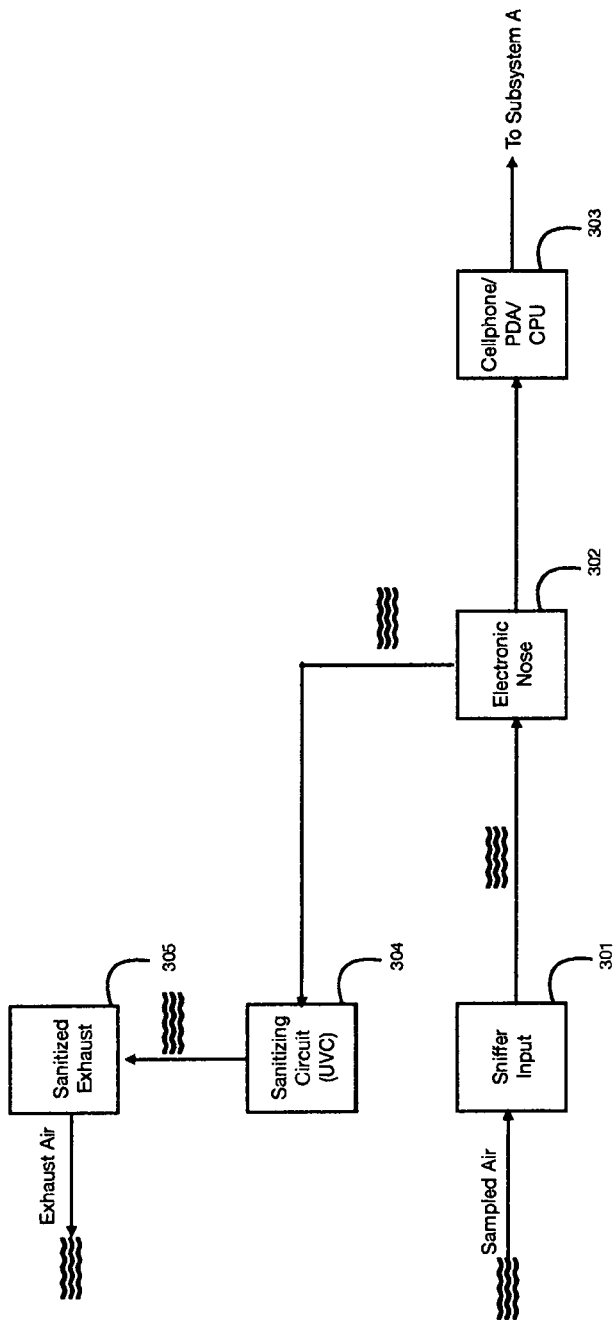

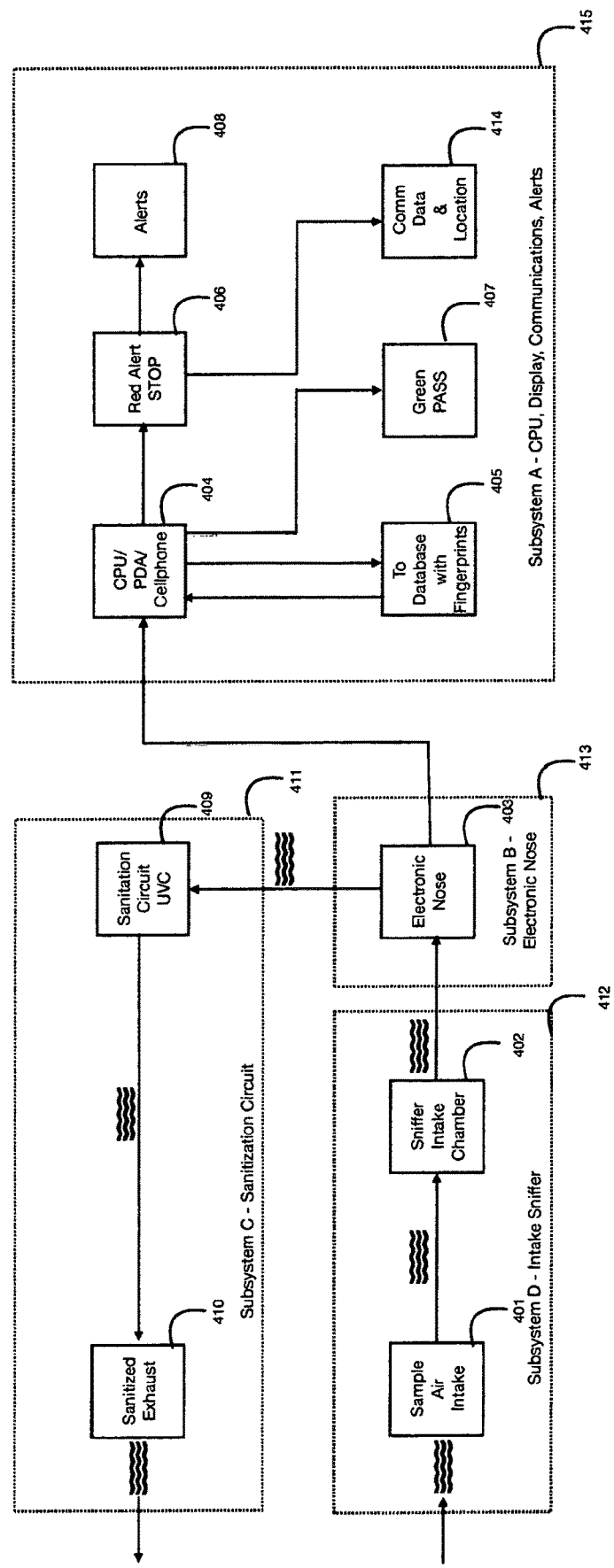

ELECTRONIC COVID, VIRUS, MICROORGANISMS, PATHOGENS, DISEASE DETECTOR

FIELD

This device is the combination of diverse technologies with "on the shelf hardware, technology, and equipment" for specific use to to detect molecular signatures and unique fingerprints of COVID-19, other pathogens, human functional disorders, and substance's fingerprints as discussed further, stated, and defined.

BACKGROUND

Every pathogen, disease, disorder, microorganism, substance, and cancer has a unique molecular signature, herein will be referred to as odors, that is given and/or sloughed by unique odors of which some are detectable by the human nose, some detected by other species with higher olfactory organs, such as a dog or pig. However, and "electronic nose" can detect disorders and pathogens that humans and dogs cannot detect, and is typically 100% accurate. The electronic nose has a theoretical potential detecting every substance, and pathogen on Earth, and space itself. The unique orders of each molecular signature will be referred to as "fingerprints" because even the slightest and simplest molecular change will change the fingerprint of what is being sniffed and sampled. This device uses existing on the shelf hardware for the specific use of sniffing and identifying all pathogen, disease, disorder, microorganism and cancer and all of the variants by subtypes and strains hereafter referred to as molecular signatures. These molecular signatures will be digitized and loaded into the database software. As the sampled air passes through the electronic nose, there will be instant lookup on the database. An alert will be given if the fingerprint on the database is detected. This device will fill the immediate need for instant and accurate COVID testing in lines, business offices, public transportation, restaurants, public recreation, military, and all businesses, as it will provide instant and accurate identification of COVID-19 or any fingerprint loaded into the database. Furthermore, the database is virtually unlimited because detecting a specific fingerprint is simple as opposed to all of the fingerprint, artificial intelligence and facial recognition systems. Additionally, the fingerprints of all illegal drugs, pathogens, and illegal trafficking can be detected without Search & Seizure violations. Since this device is noninvasive, there will not be any privacy and human rights violation, as it is sampling air and ambient air to detect the presence of fingerprints in the database. The evolution of this product is to simply identify the fingerprints of what is to be detected, then adding it to the database. The electronic nose is already proven technology.

SUMMARY

The use of this combination of existing proven technology in this combination for specific application is unique, novel, an improvement, not obvious, not statuary, improvement in the application for this use as previously discussed in the Summary by using the technology in combination to detect COVID-19 and other molecular fingerprints. The combination of the technologies are useful in many areas of public health, medicine, diagnostics, national security, Customs & Immigration without jeopardizing privacy and personal rights, and has an immediate need for public health and containment of infected and contagious people and animals because of the noninvasive nature of this device. This device can be made within combination of existing hardware, or can be reduced it in size by making the device into one package.

The embodiment can be individual existing hardware current available, it can be cluttered together into a self contained "box" using a cell phone display for visual display, or the technologies can be combined and contained into one new custom made single device with/without a PDS (Power Distribution System) as a portable molecular fingerprint detector.

An example of the functionality is that the device will be able to identify and detect each passenger boarding an airplane to ensure that there are no contagious fingerprints of the passengers being boarded. Another example is a physician giving early diagnosis of a disease before the patient has symptoms. The diagnosis will be more accurate the current day practicing best guess based on observable symptoms. A portable units will allow businesses to have safe workplace, and business owners can better ensure that the establishment can provide a safe customer experience.

This portable device does not require specialized licensing and training, as the deice will be "smart" and always incorporate the latest technological advancement and miniaturization since its components are always advancing with product evolution. Since this device is noninvasive and has known proven technology, regulation should be unnecessary.

BRIEF DESCRIPTION OF THE DRAWINGS

The invention will be better understood and objects other than those set forth will become apparent when consideration is given to the following detailed description thereof. Such description makes reference the annexed drawing within:

FIG. 3 is the Software Architecture Schematic of the Sanitation Circuit (Subsystem B).

FIG. 4 is a Functional Drawing of Subsystem B, C, & D interworking of the integrated subsystems.

DETAILED DESCRIPTION

In the following detailed description, the device embodies the combination of three major existing and proven technologies for a specific and unique use and application that is unique, novel, not obvious, not statuary, improvement in the application for this use to detect molecular signatures and unique molecular fingerprints of COVID-19, other pathogens, human functional disorders, and substance's fingerprints loaded into a database of identified and defined odors that will be either analog or digital added identifiable odors into the database. It should be noted that although the mobile phone is described the teachings of this application it can be also can be used in any other electronic device such as other electronic portable devices, such as laptops, PDAs, mobile communications terminals, media players, navigation devices, cameras, electronic books and notepads and other electronic devices offering access of information and communications. The use of a CPU is ubiquitous throughout the electronic industry. The CPU of the mobile phone will be used at the core software embodying the software application, interface drivers of the electronic, and processing the lookup and matching analog and/or digital molecular fingerprints. The database of identified and defined odors will be input and stored in the database memory in the mobile device and/or device memory and managed by readily available or custom database application.

The Electronic Nose is also ubiquitous in many fields of research, and "sniffing" use, and its software drivers are readily available. Although the Electronic Nose is used for detecting odors, it has never been used for the use of detecting pathogenic odors in a permeant unit or hand held portable unit to detect molecular signatures and unique molecular fingerprints of COVID-19, other pathogens, human functional disorders, and substance's fingerprints described in this document.

The use of the UVC is well known to be germicidal, but limited primarily to photo therapy and experimental use.

Since the existing technologies are proven and ubiquitous, they will not be described in detail, but only their functionality will be referred.

Figure 1:
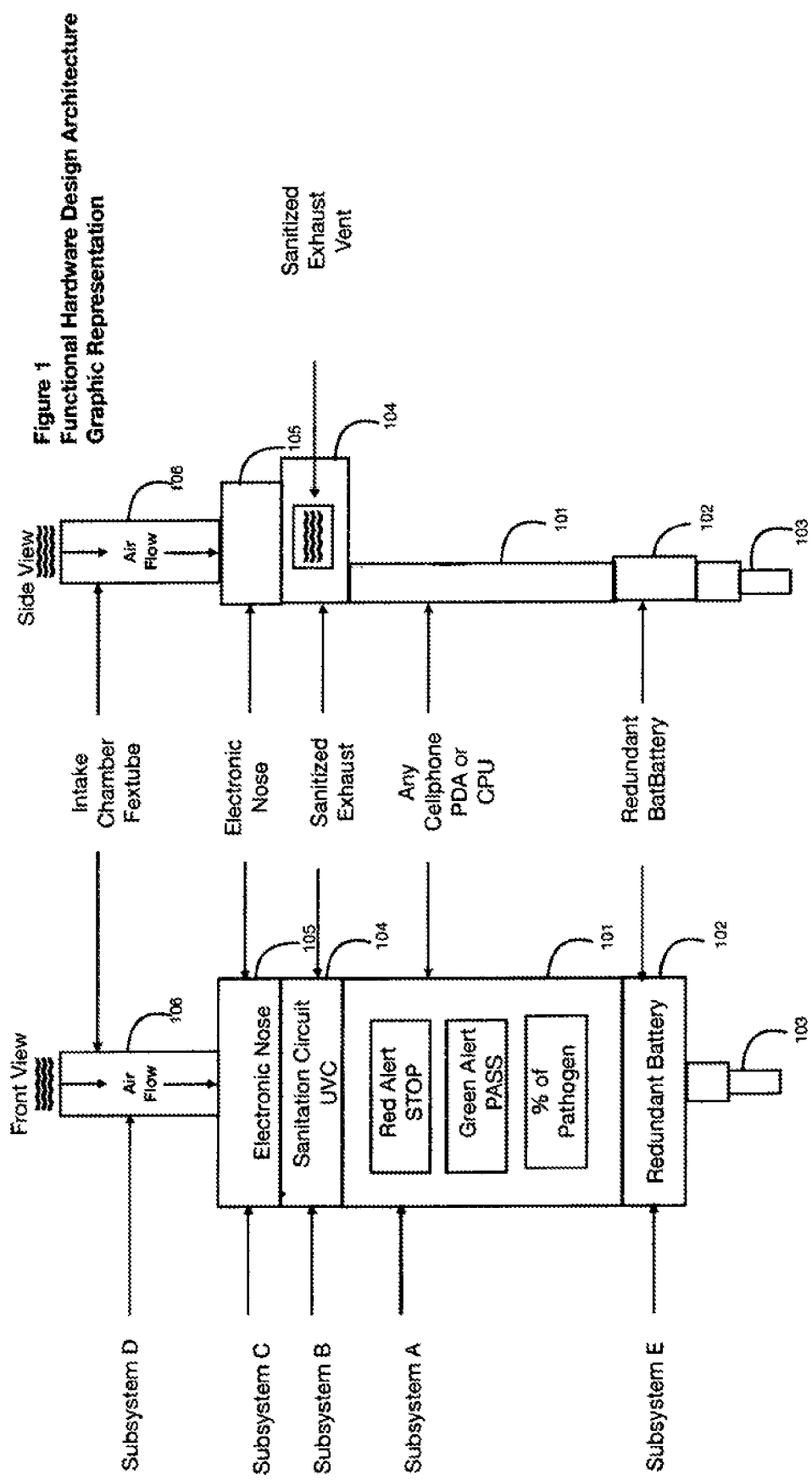
FIG. 1 is a Graphic Representation of the Functional Hardware Design Architecture of the subsystem components of the integrated device carrying out the method of the invention.

FIG. 1 is the functional hardware diagram of a mobile terminal 101 connected to the electronic nose 105 that will identify the fingerprints of an odor and match it to the defined odors in the database, and will give an alert that is safe with a green visual indication on the mobile device for an individual to pass, or give an red alert with the detected odor fingerprint in the sampled intake airflow through the Intake Camber Sniffer 106. This schematic shows the airflow through the Electronic Nose, passing through the germicidal UVC 104 and sanitized exhaust of both the sampled air and heat from the electronic Nose and UVC. Any mobile device can be used as the CPU, application driver, interface drivers, and database storage. This functional drawing also shows the battery 102 for portable usage, and/or reserve power. The External 18 VDC input cord 103, is a standard mini USB power cord to supply power to the mobile device/CPU 101, UVC 104, and electronic nose 105.

It must be understood that each odor must be obtained and identified by Gas Chromatography before entering into the database embodied within the mobile device/CPU 101.

Figure 2:
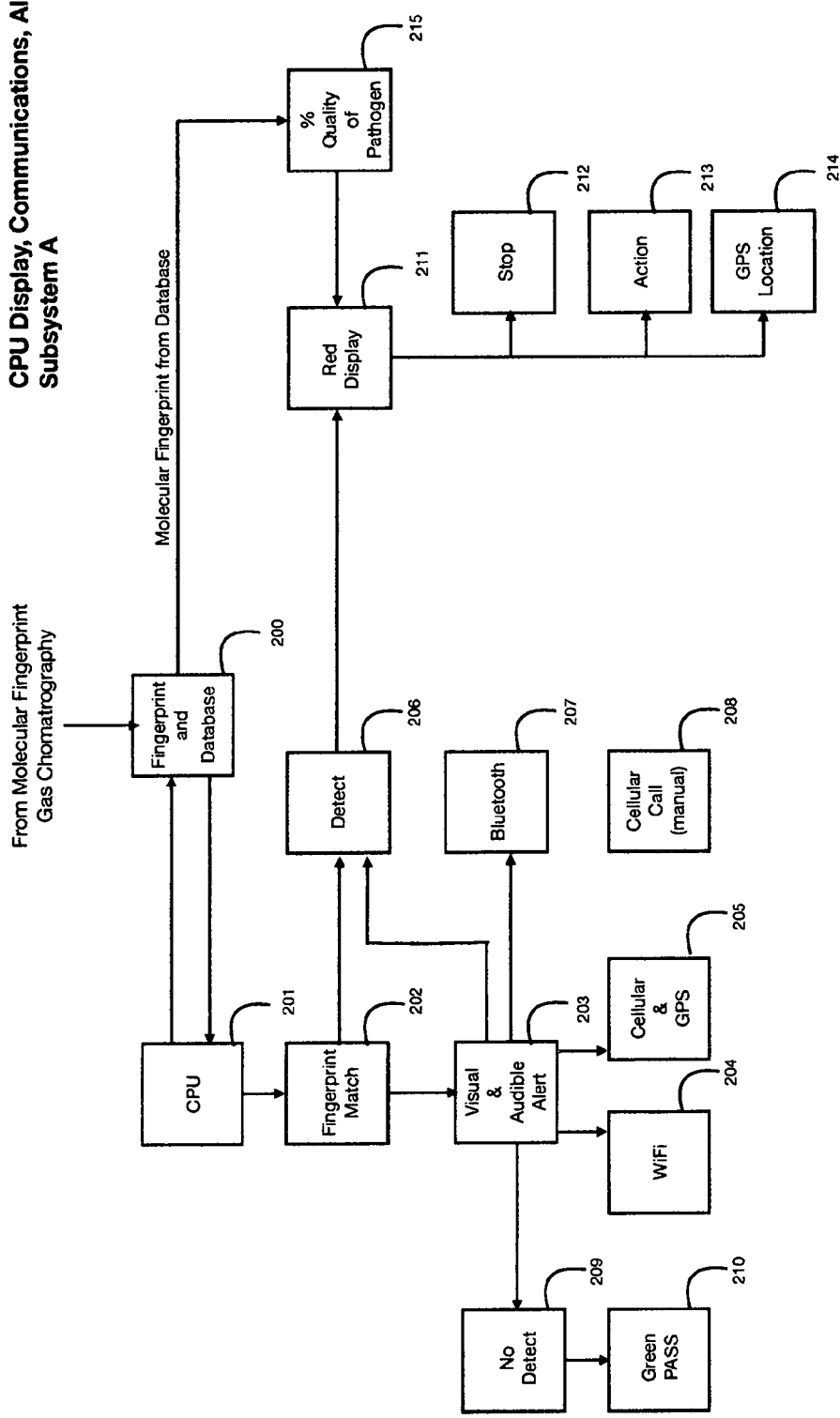
FIG. 2 is the Software Architecture Schematic of the CPU Display, Communications, Alerts (Subsystem A).

FIG. 2 is a functional Software Architecture Schematic of the Display and Communication Subsystem A. When the electronic nose detected a molecular fingerprint previously input into the database, the CPU signal will flow per FIG. 2 as follows. If there are no detected molecular fingerprints, the signal will go to No Detect 209, and keep the Green/Pass 209, and illuminate the Green/Pass 210 visual display.

A detected fingerprint from the molecular fingerprint Detect 200 will send the signal to the CPU 201, which is Subsystem B. If there is a matched detected 202, there will be a Red Alert. The Red Alert will activate an Audible Alert 203 and notify 203 the response guardian and all authorities having jurisdiction (AHJ) via WiFi 204, Cellular and GPS 205. The Audible Detect 203 will also initiate a Cellular Call 209 for immediate coordination of all AHJs for safety remediation, and Cellular talk channel to other mobile devices and/or landline calls. Detect 202 will also send reports to any PC, mobile device, or printer the incident, GPS coordinates, and physical location of the detection via Bluetooth 208 within range.

In addition, Fingerprint Detect 202 will Activate a Visual Red Alert 206 to Red Display on the mobile device/CPU screen. The Red Display 211 will advise the safety guardian and AHJs to stop 212 an an individual, take action 213 action per predetermined procedures, and simultaneous will display the location 214 per GPS coordinates.

The molecular Finger Detect 200 will also display the Quantity of Identified fingerprint 215 per database identified ranges, for example first strain COVID-19 acceptable range of finger print will indicate if the pathogen is in its infancy stage, peak stage, or near the end stage.

FIG. 3 is a Software Architecture of the Sanitation Circuit, Subsystem B. This subsystem contains redundant UVC radiation bulbs that will kill or deactivate identified fingerprints return into the ambient air for two purposes. 1) the eliminate the possibility of returning contaminated air containing the identified fingerprint or pathogen into the ambient air that could make false positive alerts, and, 2) if the pathogen is a contagion, it will reduce the risk of spreading the sniffed air which may be contagious or dangerous to others. The UVB subsystem will contain redundant UVB radiation bulbs should one have a fault. In addition, there could be redundant fans to 1) bring intake air through the system, and 2) exhaust sanitized return air and heat from the electronic nose 105 and UVC 104. Note: According to multiple sources (NASA, FDA, and others) the wavelengths of the UVA, UVB and UVC regions are as follows:

UVA 400 nm-320 nm

UVB 320 nm-290 nm

UVC 290 nm-100 nm

Sample air will be from the Intake Chamber Sniffer 301, into the electronic nose 302. The electronic nose will be managed by the CPU/Cellphone or PDA 303, through the UVC Sanitizing Circuit 304, and out the Sanitation Exhaust 305 into the ambient air.

Subsystem B is the Exhaust System 410 within the Sanitizing Circuit 411. It contains redundant fans to provide intake ambient air 401 through the Sniffer Intake Chamber 402 within the Sanitizing Subsystem B 412. The airflow passes to the Subsystem C 413 Electronic Nose 403, which identifies the molecular fingerprint, and sends the fingerprint to be processed by the CPU/Mobile device. The airflow passes from the Electronic Nose to the Sanitizing Circuit UVC 409 which will kill and or deactivate the odor being sniffed, and on through the Exhaust System 410 to return to the ambient air.

The Electronic Nose 403 will send the information to Subsystem A CPU/mobile device 404. The information from the Electronic Nose 403 will be processed by the CPU 404 embodied within Subsystem A, The CPU 404. Function goes from the CPU 404, to the Database 405 with preloaded and defined odor molecular fingerprints that are obtain from gas chromatography. If there is no matched molecular fingerprint, the CPU 404 will send a signal for the Green/Pass 407 light to remain in the on visual display the green light on the mobile unit visual display. However, if a molecular fingerprint is detected by matched database lookup, the CPU 404 will deactivate the Green/Pass visual display 407, and activate the Red Alert 406 on the visual display on Subsystem A for the Display Communication and Alerting Process on FIG. 2 Subsystem, CPU 201.

ADDITIONAL BACKGROUND OF THE INVENTION

The inventor was born with Primary Immune Deficiency with the ability to smell different disease, microorganisms, pathogens, and viruses. Being in the electronics industry for 40 years and evolution of electronics and high tech, the inventor has assembled a variety of technologies that will detect COVID and variant strains, other microorganisms, pathogens, and diseases, including cancers.

The Emirati government has trained dogs to sniff people with the COVID virus, and for use entering airplanes before flight. Therefore, if I can smell certain pathogens, and dogs can be trained to detect pathogens, then an electronic device can also detect the pathogens more accurately and faster than mammals.

There are supporting documents of DoD developing an electronic people sensing device in the Vietnam War to detect the presence of humans in caves, manholes, and in the jungle. It was developed by General Electric and was thus awarded the patents which have long expired, and entitled as "The Forgotten Weapon."

This new device is a new specific application that is new and novel using newer technology many diagnostic applications using smells. Every smell has a unique fingerprint or molecular scent. This device will use an electronic nose to collect the emitted scent, match to a database of programmed scents, and identify whether the smell of a person has a pathogen, identify which pathogen, measure the amount of the pathogen to determine stage, and send immediate alerts and communicate to other identified location to take appropriate and immediate action.

This device is very much like the "Tricorder" detection device on Star Trek where the spaceship physician can give immediate diagnosis of any ailment. Specifically, this device will use smell to detect COVID, any variant, other viruses, pathogens, diseases, and even cancers theoretically with 100% accuracy at 100% of the time.

Electronic COVID, Virus, Microorganism, Pathogen, Disease, Detector

This device is a combination of technologies for new and novel utility device that will use odor unique molecular signature/fingerprint to detect and measure COVID, any individual strain, virus, microorganism, pathogen, disease, or cancer. This device has a theoretical 100% accuracy at 100% of the time.

This device will have an intake air sample of breath or natural body odor to detect molecular signature/fingerprint. The sample will use an "electronic nose" to detect the specific molecular signature against a database. Upon a positive signature match with the database, the CPU device will send a visual and audible alert, as well as communications to designated stations or immediate action and reporting to authorities having jurisdiction.

This device will be able to detect other non-invasive molecular signatures of other odors, such as decomposing bodies, and diagnosis of several diseases and conditions that are listed in the database.

There are five subsystems in this hand held or mounted device:

Subsystem A—a preprogrammed wireless phone or other CPU as the central processing unit to match molecular signature within the intake air. The CPU will match the molecular signature with the database. If there is a match, the device will send a pass/go alert, activate designated communications via Bluetooth, cellular, WiFi, or other transmission technologies. The CPU will also record quantity readings to determine viral shed, age, and stage of the virus or pathogen to determine stage of the pathogen.

Subsystem B—is a sanitation circuit consisting of either UVB high frequency or ozone to sanitize the out flow air to prevent false positives reading from previous samples or from ambient air. The UVC will sanitize and/or deactivate all of the outflow air.

Subsystem C—is an electronic nose that will sample intake air samples. The "electronic nose" will send detected molecular signatures to match against the programmed database. This requires an application to interface the CPU/cellphone device, and have instant look in the database resident in the CPU/cellphone device.

Subsystem D—is a flexible or rigid tube that intakes the odorous air from either breath and/or body odors. It is a passive and noninvasive device.

Subsystem E—is external power supply, battery, redundant battery, and communications ports. The communication and external alarms can be any wireless transmission, Ethernet, alarm wiring, infrared, or microwave transmission technology. The device can be portable or connected to fixed power.

INDEX OF FIGURE NUMBERS

FIG. 1 Functional Hardware Design Architecture, Graphic Representation
    101—Any Cell Phone, PDA, CPU
    102—Redundant battery
    103—Power Cord
    104—Sanitizing Circuit
    105—Electronic Nose
    106—Intake Chamber, flextube
FIG. 2 Software Architecture Schematic, CPU Display, Communications, Alerts
    200—Fingerprints and Database
    201—CPU (cellphone, PDA)
    202—Fingerprint match
    203—Visual and Audible Alerts
    204—WiFi Connection
    205—Cellular and GPS (location)
    206—Detect Fingerprint Match
    207—Bluetooth connection to printers and other nearby devices
    208—Cellular/Wireless call (manually)
    209—No Detect (molecular fingerprints)
    210—Green PASS visual Display
    211—Red Display
    212—STOP
    213—Action
    214—GPS (Location)
    215—% Quality of Pathogen
FIG. 3 Software Architecture Schematic, Sanitation Circuit
    301—Sniffer Input
    302—Electronic Nose
    303—Cellphone/PDA/CPU
    304—Sanitizing Circuit
    305—Sanitized Exhaust
FIG. 4 Functional Drawing, Subsystems B, C, & D
    401—Sample Air Intake
    402—Sniffer Intake Chamber
    404—CPU/PDA/Cellphone or Wireless Device
    405—To Database with Fingerprint
    406—Red Alert STOP Display
    407—Green PASS Display
    408—Alerts
    409—Sanitation Circuit with UVC
    410—Sanitized Exhaust
    411—Subsystem C—Sanitation Circuit
    412—Subsystem D—Intake Sniffer
    413—Subsystem B—Electronic Nose
    414—Communications, Data, and Location (GPS)
    415—Subsystem A—CPU, Displays, Communications, Alerts

The invention claimed is:

1. A molecular signature detection system comprising:
a first subsystem is an electronic device comprising a central processing unit (CPU) and a database of molecular signatures, wherein the CPU processes a lookup and matching of a molecular signature sampled and detected by an electronic nose to identify whether there is a match with a molecular signature stored in the database, the molecular signature indicating presence of an odor associated with molecular fingerprints of COVID-19 and variant strains, viruses, bacteria, pathogens, microorganisms, dysfunctional disorders having a molecular signature, cancers by type, explosives, illegal drugs, and/or substances with a detectable odor;
a second subsystem comprising a sanitation circuit including Ultraviolet C (UVC) (290 nm-100 nm) or Ultraviolet B (UVB) (320 nm-290 nm) radiation bulbs capable of sanitizing and/or deactivating outflow air to prevent false positive readings from air samples passing through the sanitation circuit or from ambient air;
a third subsystem comprising the electronic nose that samples intake air samples and passes detected molecular signatures through to the second subsystem to be processed by the CPU to look up and match against molecular signatures stored in the database in the first subsystem;
a fourth subsystem comprising a tube that intakes odorous air from breath and/or body odors of an individual, chemical, organism, or substance and transmits the intake air to the electronic nose in the third subsystem for sampling; and
a fifth subsystem comprising an external power supply, a battery, a redundant battery, and one or more communications ports, wherein the fifth subsystem powers at least the first subsystem and the third subsystem,
wherein the first subsystem has an alert system that provides a visual indication on the first subsystem whether the individual is safe to pass when there is no match in the database or should be stopped when there is a match in the database, and
wherein each of the molecular signatures in the database are identified by gas chromatography before being entered in the database.

2. The system of claim 1, wherein the first subsystem CPU records quantity readings to determine viral shed, age, and stage of the molecular fingerprints of COVID-19 and variant strains, viruses, bacteria, pathogens, microorganisms, dysfunctional disorders having a molecular signature, cancers by type, explosives, illegal drugs, and/or substances with a detectable odor.

3. The system of claim 1, wherein the system is a fixed, a portable or a handheld device.

4. A molecular signature detection system comprising:
an electronic nose that samples intake airflow from breath and/or body odor of an individual or any substance to identify molecular signatures; and
a mobile terminal connected to the electronic nose, the mobile terminal comprising:
a database containing a plurality of molecular signatures associated with defined odors, each of the plurality of molecular signatures identified by gas chromatography before being entered into the database, the molecular signature indicating presence of an odor associated with molecular fingerprints of COVID-19 and variant strains, viruses, bacteria, pathogens, microorganisms, dysfunctional disorders, cancers by type, explosives, illegal drugs, and/or substances with a detectable odor;
a central processing unit (CPU) that receives the molecular signatures identified in the intake airflow from the electronic nose and processes to look up match against molecular signatures stored in the database to identify whether there is a match in the database; and
an alert system that provides a visual indication whether the molecular signatures identified in the intake airflow match one or more of the plurality molecular signatures in the database.

5. The system of claim 4 further comprising:
a sanitation circuit through which the sampled air flow passes from the electronic nose to the mobile terminal, the sanitation circuit containing Ultraviolet C (UVC) (290 nm-100 nm) or Ultraviolet B (UVB) (320 nm-290 nm) radiation bulbs that deactivate identifiable molecular fingerprints in the database and/or all contaminants to return into ambient air.

6. The system of claim 4, wherein the alert system provides a green/pass visual display if there is no match and a red visual display and audible alert when there is a match.

7. The system of claim 4, wherein the alert system notifies personnel associated with the system.

8. The system of claim 6, wherein the audible alert initiates a cellular, Bluetooth, and/or Wi-Fi transmission for coordination of personnel associated with the system.

9. The system of claim 6, wherein when there is a match, one or more reports are sent to personnel associated with the system using Bluetooth, Wi-Fi, and/or cellular transmission to provide information about the match, the information including GPS coordinates and physical location.

10. The system of claim 4, wherein the CPU records quantity readings to determine viral shed, age, and stage of the molecular fingerprints of COVID-19 and variant strains, viruses, bacteria, pathogens, microorganisms, dysfunctional disorders, cancers by type, explosives, illegal drugs, and/or substances with a detectable odor.

11. The system of claim 4 further comprising:
a tube that intakes the airflow from breath and/or body odor of the individual to be sampled by the electronic nose,
wherein the tube is a solid or flex tube.

12. The system of claim 4 further comprising:
an external power supply;
a battery;
a redundant battery; and
one or more communications ports.

13. The system of claim 4, wherein the system is stationary, portable, or handheld.

* * * * *